(12) United States Patent
Umebayashi et al.

(10) Patent No.: US 7,383,865 B2
(45) Date of Patent: Jun. 10, 2008

(54) WELDING DEVICE

(75) Inventors: Toyoshi Umebayashi, Osaka (JP);
Kikuo Yoneoka, Osaka (JP)

(73) Assignee: Zuiko Corporation, Osaka (JP)

( * ) Notice: Subject to any disclaimer, the term of this patent is extended or adjusted under 35 U.S.C. 154(b) by 91 days.

(21) Appl. No.: 11/568,233

(22) PCT Filed: Apr. 27, 2005

(86) PCT No.: PCT/JP2005/007986

§ 371 (c)(1),
(2), (4) Date: Oct. 24, 2006

(87) PCT Pub. No.: WO2005/105410

PCT Pub. Date: Nov. 10, 2005

(65) Prior Publication Data
US 2007/0251643 A1    Nov. 1, 2007

(30) Foreign Application Priority Data
Apr. 30, 2004 (JP) ............................ 2004-135063
Aug. 10, 2004 (JP) ............................ 2004-233055

(51) Int. Cl.
*B32B 37/00* (2006.01)
(52) U.S. Cl. .................. 156/350; 156/510; 156/580.2
(58) Field of Classification Search ............... 156/350, 156/359, 510, 553, 555, 580, 580.1, 580.2, 156/581, 582, 583.1; 700/302
See application file for complete search history.

(56) References Cited

U.S. PATENT DOCUMENTS 5,660,679 A * 8/1997 Rajala et al. ............. 156/580.1
5,711,847 A * 1/1998 Rajala et al. ............. 156/580.2

FOREIGN PATENT DOCUMENTS

| GB | 2 257 652 | 1/1993 |
|---|---|---|
| JP | 04-006010 | 1/1992 |
| JP | 05-015551 | 1/1993 |
| JP | 06-009927 | 2/1994 |
| JP | 10-513128 | 12/1998 |
| JP | 2001-151208 | 6/2001 |
| JP | 2004-330622 | 11/2004 |
| WO | 96/23645 | 8/1996 |

OTHER PUBLICATIONS

International Search Report for corresponding Application No. PCT/JP2005/007986 mailed Jul. 26, 2005.

* cited by examiner

*Primary Examiner*—James Sells
(74) *Attorney, Agent, or Firm*—Renner, Otto, Boisselle & Sklar, LLP

(57) ABSTRACT

The present welding device is a device for welding webs W, the device including: a drum 20 and an anvil 21 rotating about an axis; a transfer section 22 provided on a periphery of the drum 20 to rotate together with the drum 20; a horn 11 which, together with the anvil 21, applies a vibration energy to a layered portion of the webs; a cutter 30 which comes into contact with the anvil 21 to cut the webs; a sensor 40 for measuring a distance between the anvil 21 and the horn 11; and a control section for controlling a relative positions of the anvil 21 and the horn 11 based on the measured distance between the anvil 21 and the horn 11 as measured by the sensor. While the horn 11, together with the anvil 21, applies the violation energy to the webs W, the cutting of the webs W by the cutter 30 is not performed.

5 Claims, 5 Drawing Sheets

WELDING DEVICE

TECHNICAL FIELD

The present invention relates to a welding device for welding a plurality of webs together by applying ultrasonic vibrations to the webs layered together into a sheet-like material.

BACKGROUND ART

In a packaging device of the first patent document identified below, a sealing device and a cutter are separate from each other. In this device, since the cutter and the sealer are separate from each other, a phase shift (displacement) occurs therebetween, lowering the precision of the positional relationship between a sealed area and a cut portion.

In the fusing device of the second patent document identified below, a disc-shaped ultrasonic horn and a cutter are provided around a single drum. Therefore, fusion cannot be done in a direction along the rotation axis of the drum. Moreover, the second patent document fails to disclose performing the welding by ultrasonic vibrations and the cutting by a cutter at staggered times.

In the fusing device of the third patent document identified below, a heat sealer and a cutter are provided around a single drum. However, the device of the third patent document is not for applying ultrasonic vibrations to a sheet-like material.

[First Patent Document] Japanese Laid-Open Patent Publication No. 2001-151208 (paragraphs 0005 and 0006, FIG. 7)

[Second Patent Document] Japanese Laid-Open Utility Model Publication No. 06-009927 (paragraphs 0020 to 0022, FIG. 1)

[Third Patent Document] Japanese Laid-Open Patent Publication No. 4-6010 (claims, upper-right column of page 3, FIG. 1)

DISCLOSURE OF THE INVENTION

An object of the present invention is to provide a welding device, which is capable of achieving a high precision of the positional relationship between a welded area and a cut portion, and is capable of preventing the precision of the application of ultrasonic vibrations from lowering due to the vibration from cutting.

A welding device of an aspect of the present invention is a welding device for welding a layered portion where a first web and a second web are layered together, the welding device including: a drum rotating about an axis; a transfer section provided on a periphery of the drum to rotate together with the drum for transferring the first and second webs while holding the first and second webs thereon; an anvil provided on the periphery of the drum and extending generally in a direction of the axis for rotating together with the drum; a horn provided close to the periphery of the drum, which, together with the anvil, applies a vibration energy to the layered portion; a cutter provided close to the periphery of the drum, which comes into contact with the anvil to cut the first and second webs; a sensor for measuring a distance between the anvil and the horn; and a control section for controlling a relative positions of the anvil and the horn based on the measured distance between the anvil and the horn as measured by the sensor, wherein while the horn, together with the anvil, applies the vibration energy to the first and second webs, the cutting of the first and second webs by the cutter is not performed.

In this aspect, both the horn and the cutter are provided in proximity to the periphery of a single drum, which is provided with an anvil and a transfer section. Therefore, it is possible to apply ultrasonic vibrations to the webs on an anvil and then the webs can be cut on the same anvil, thereby improving the precision of the positional relationship between the welded area and the cut portion.

In a welding (sealing) process using ultrasonic vibrations, mechanical vibrations are ultrasonically transmitted to a horn (vibrator), and a thermoplastic web is passed through between a horn and an anvil while being under pressure, whereby the web is welded by the frictional heat. Therefore, if the welding by the horn and the cutting by the cutter take place simultaneously, the vibration caused when the cutter contacts (hits) the anvil may vary the interval (gap) between the horn and the anvil, i.e., the distance therebetween. Whether the interval is varied or not, such a vibration by the cutter may cause a malfunction of the sensor for measuring the interval.

In view of this, the welding device of this aspect does not perform the cutting by the cutter and the welding by ultrasonic vibrations from the horn simultaneously, but performs these operations at different times. Thus, even though the welding and the cutting are performed on the same drum, it is possible to prevent lowering of the reliability of the welding by ultrasonic vibrations.

Thus, the welding device of this aspect can prevent poor welding which may occur when the distance between the horn and the anvil varies, and malfunctioning of the sensor for measuring the distance between the horn and the anvil, because the vibrations by the cutting do not occur during the welding.

With the present welding device, the frequency (the period) of the ultrasonic vibrations is not limited to any particular number, and it can be, for example, about 15,000 to 20,000 cycles per second.

In the present welding device, the anvil may include a first portion and a second portion for receiving vibrations from the horn, and a third portion for receiving the cutter, the third portion being located between the first portion and the second portion, and the first portion, the third portion and the second portion may be arranged in this order in a circumferential direction of the drum.

By providing the first portion, the second portion and the third portion in such a manner, it is possible to reliably cut the sheet-like material between two welded areas.

However, the present invention is not limited with respect to the relationship between the welded position and the cut position in the sheet-like material including a plurality of webs, and the sheet-like material may be cut along the end (edge) of the welded area. In the present invention, the sheet-like material may be cut into pieces so that the pieces of the material can be separated, or a portion may be cut out of the sheet-like material.

In the present welding device, a distance from a center of rotation of the anvil to the first portion may be generally equal to a distance from the center of rotation to the second portion. This makes it easier to control the gap between the horn and the anvil, thus enhancing the reliability of the welding process.

In the present welding device, a distance from a center of rotation of the anvil to the first portion and that from the center of rotation to the second portion may be longer than that from the center of rotation to the third portion.

With such distance settings, the web is not fused in the third portion, whereby the webs will not be hardened in the third portion. Therefore, the cutter can easily cut the webs in the third portion.

In the present invention, there may be a plurality of horns, and the same location of the sheet-like material may be welded over and over by the plurality of horns.

Where the sheet-like material rotates together with the drum, the sheet-like material on the anvil comes close to, and is heated by, the plurality of horns successively. Thus, since the same location of the sheet-like material is welded by the plurality of horns, it will be possible to allow for an amount of time necessary for the welding. Therefore, it is possible to increase the speed at which the sheet-like material is transferred.

However, the present invention is not limited with respect to the number of horns, and there may be provided one horn or a plurality of horns.

In the present invention, a plurality of anvils may be provided at a regular pitch (be equally spaced) along the periphery (outer circumference) of the drum so that the welding by ultrasonic vibrations can be done when the horn faces the anvil. In such a case, the angle (central angle) between the cutter roller and the horn may differ from the angular pitch between the anvils so that the welding by ultrasonic vibrations and the cutting by the cutter are not performed simultaneously.

With such an arrangement of the cutter roller, the horns and the anvils, during the welding process where a horn is facing an anvil, none of the other anvils are facing the cutter roller. That is, the cutting is not performed when the welding is performed.

When the sheet-like material is sandwiched between the horn and the anvil, and an energy from ultrasonic vibrations is applied to the sheet-like material, the plurality of webs are thermally fused together. Thus, the interval between the horn and the anvil is preferably on the order of μm to 10 μm. Therefore, the anvil is preferably protruding radially outward with respect to other portions of the drum. The present invention may also employ a structure where the anvil and the horn come close to each other when applying ultrasonic vibrations.

The drum may be provided with a plurality of transfer sections for holding the sheet-like material thereon, and anvils may be provided between the transfer sections. The number of transfer sections and the number of anvils may each be one or plural.

In the present invention, the sheet-like material may be a semi-finished product including a plurality of webs layered together, and the welding device may weld the webs together so as to divide the semi-finished product into individual products. An absorbent body core may be provided between the plurality of webs.

The final product to be produced by the present invention may be disposable worn articles, such as disposable underpants, diapers, and sanitary products.

DESCRIPTION OF THE REFERENCE NUMERALS

Figure 1:
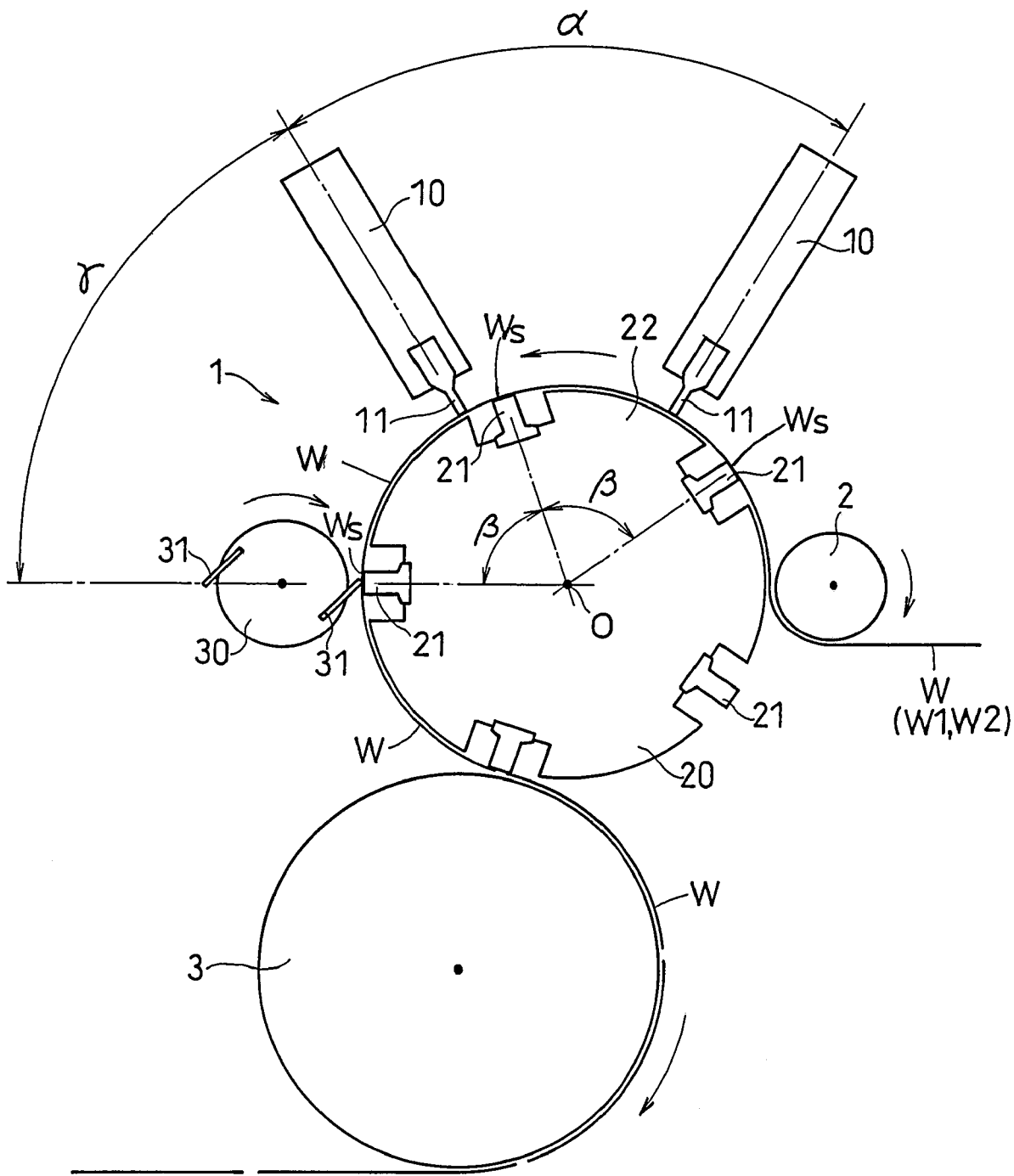
FIG. 1 is a schematic layout diagram showing a processing device including a welding device according to one embodiment of the present invention.

1: Welding device
11 (11a, 11b): Horn
20: Drum
21: Anvil
22: Transfer section
30: Cutter roller
40: Measurement section (sensor)
41: Control section
a1: First portion
a2: Second portion
a3: Third portion
$C_L$: Cut line
O: Center of rotation
W: Sheet-like material
W1: First web
W2: Second web
Ws: Target portion

BEST MODE FOR CARRYING OUT THE INVENTION

The present invention will be understood more clearly from the following description of preferred embodiments taken in conjunction with the accompanying drawings. Note however that the embodiments and the drawings are given for the purpose of illustration and explanation and should not be used to define the scope of the present invention. The scope of the present invention is to be defined by the appended claims. In the accompanying drawings, the same reference numerals denote the same or corresponding elements throughout the several figures.

An embodiment of the present invention will now be described with reference to the drawings.

FIG. 1 shows a first embodiment of the present invention.

As shown in FIG. 1, a welding device 1 transfers a continuous sheet-like material W and applies ultrasonic vibrations to a welding target portion Ws of the sheet-like material W, for example, as shown in FIG. 5(a), so as to thermally fuse the webs together at the welding target portion Ws, after which the welding device 1 cuts the sheet-like material W. For example, the sheet-like material W may be a semi-finished product. The sheet-like material W includes a first web W1 and a second web W2 laid on each other, and the webs are to be fused together at a predetermined welding target portion Ws in an area where the two webs W1 and W2 overlap with each other. For example, as shown in FIG. 5(b), webs of the semi-finished product W are welded (bonded) together in two welded areas, each being the welding target portion Ws, and then the semi-finished product W is cut along a cut line $C_L$ between the two welded areas Ws into individual articles (underpants or diapers).

As shown in FIG. 1, an apparatus for producing a worn article may include a take-in roller 2 for guiding the sheet-like material W into the welding device 1, a take-out roller 3 for guiding the sheet-like material W, which has been welded by the welding device 1, out of the welding device 1, and a transfer device (not shown) for receiving the sheet-like material W from the take-out roller 3.

The welding device 1 includes at least one ultrasonic welder 10 and a rotatable cutter roller 30 along the periphery of a drum 20 receiving the sheet-like material W. The ultrasonic welder 10 and the cutter roller 30 are provided radially outside of the drum 20. The ultrasonic welder 10 and the cutter roller 30 are spaced apart from each other in the circumferential direction of the drum 20. Each ultrasonic welder 10 includes ultrasonic wave generation means (not shown) and a horn 11. The horn 11 is provided in close proximity to the periphery of the drum 20.

The cutter roller 30 includes one or more cutters 31. The circumferential velocity of the cutter roller 30 may be about the same as, or different from, that of the drum 20. The cutters 31 are provided on the periphery of the cutter roller 30 so that the cutters 31 can come in close proximity to the periphery of the drum 20.

A plurality of anvils 21 are attached to the drum 20 with a regular angular pitch β (beta). The cutter roller 30 and the horn 11 are angularly spaced apart from each other by an angle γ (gamma). The angle γ is different from the pitch β of the anvils 21. Therefore, when one of the anvils 21 is close to (facing) the cutter roller 30, as shown in FIG. 1, none of the other anvils 21 are facing the horns 11. When one of the anvils 21 is facing the horn 11, as shown in FIG. 2, none of the other anvils 21 are facing the cutter roller 30.

As shown in FIG. 1, the welding device 1 may include a plurality of ultrasonic welders 10. The ultrasonic welders 10 may be provided radially outside of the drum 20 with a predetermined angular pitch α (alpha). The pitch α of the horns 11 and the pitch β of the anvils 21 may be the same or different from each other.

If the angular pitch α of the horns 11 and the angular pitch β of the anvils 21 are the same (α=β), the plurality of ultrasonic welders 10 can be actuated simultaneously, thereby realizing a simple control.

If the angular pitch α of the horns 11 and the angular pitch β of the anvils 21 are different from each other, when one of the anvils 21 is close to, and facing, the horn 11 of one of the ultrasonic welders 10, none of the other anvils 21 are close to, and facing, the horns 11 of the ultrasonic welders 10. Then, it is possible that the ultrasonic welders 10 do not simultaneously weld the sheet-like material W, thus preventing resonance.

Figure 3:
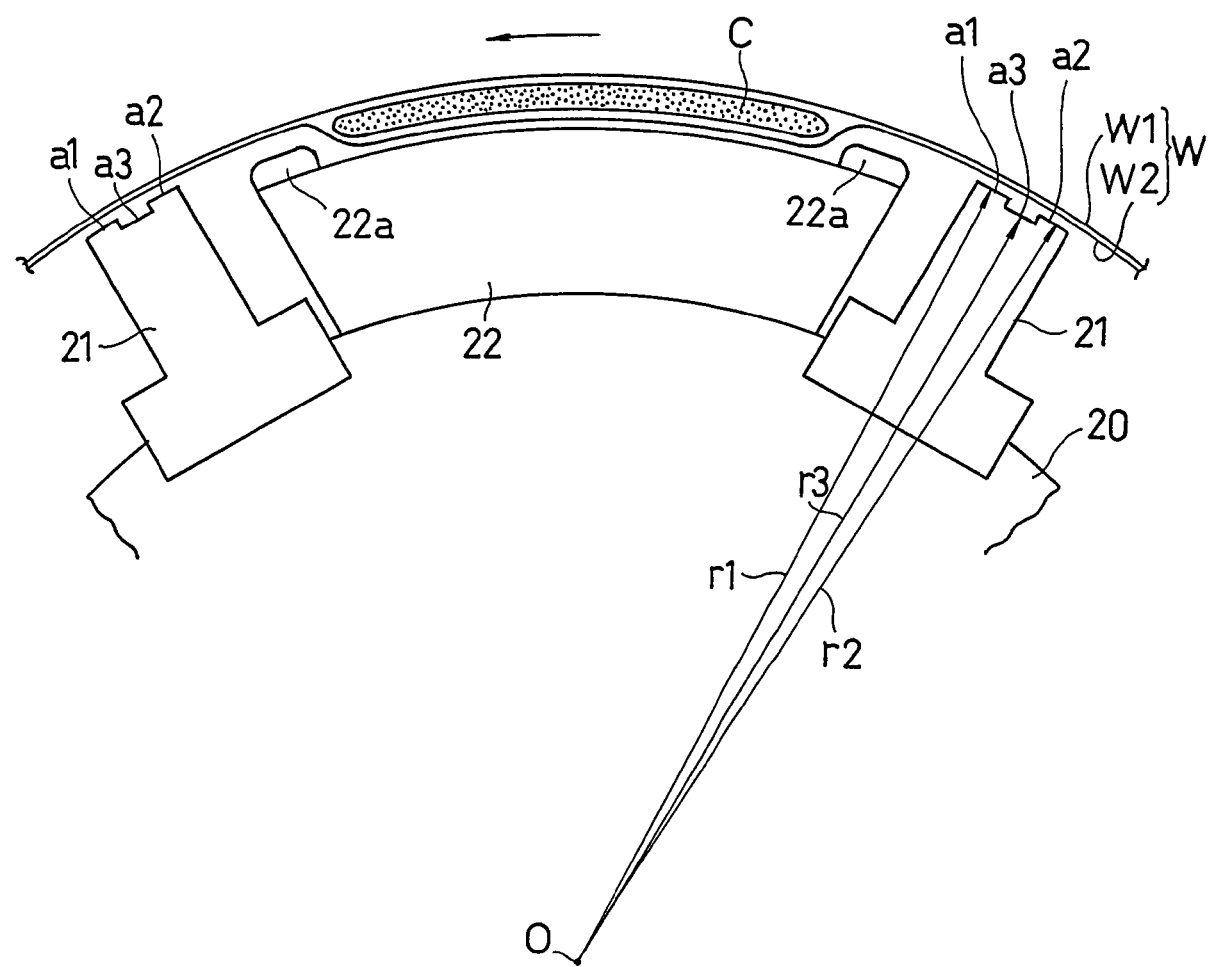
FIG. 3 is a schematic side view showing a portion of the welding device around an anvil and a transfer section thereof.

As shown in FIG. 3, the drum 20 is provided with a plurality of transfer sections 22 for transferring the sheet-like material W (the webs W1 and W2). The transfer sections 22 rotate together with the drum 20 and the anvils 21 while holding the sheet-like material W thereon, thereby transferring the sheet-like material W from the take-in roller 2 to the take-out roller 3. The transfer sections 22 and the anvils 21 alternate with each other in the circumferential direction of the drum 20, and rotate along the outer circumference of the drum 20.

It is preferred that the transfer sections 22 are so-called "pads" capable of sucking and holding the sheet-like material W thereonto by means of a vacuum. This is for preventing the horns 11 from coming into contact with, for example, a hold-down member for holding down the sheet-like material W.

Figure 2A:
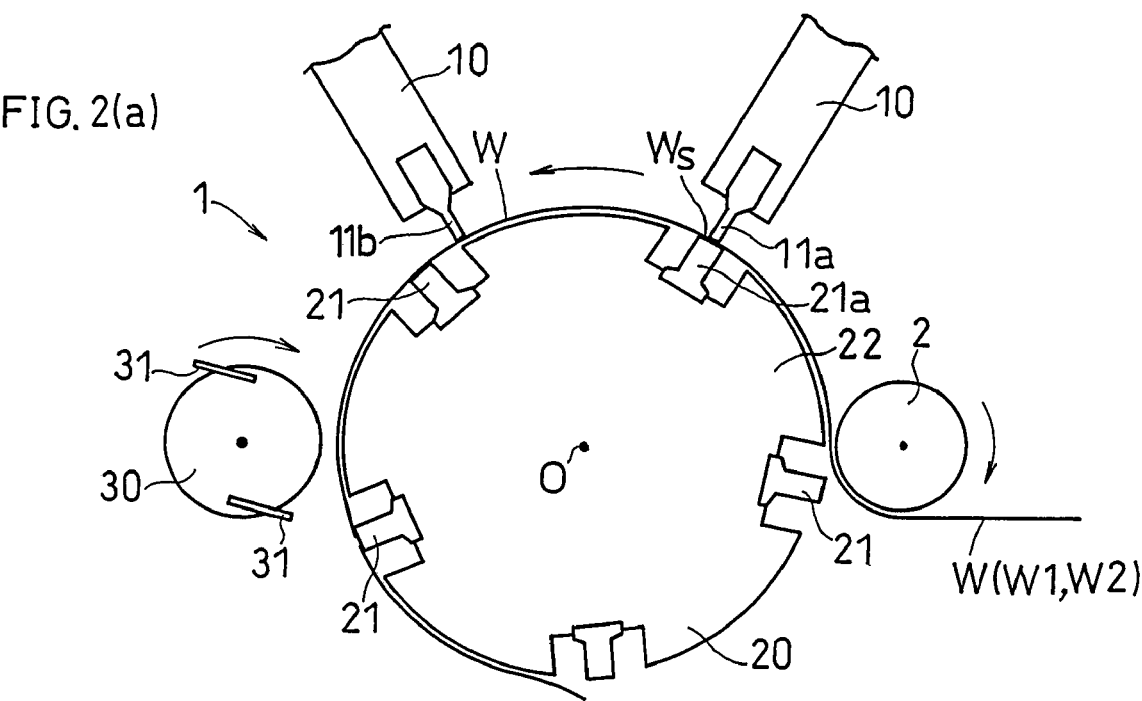
FIGS. 2(a) and 2(b) are side views illustrating the operation of the welding device.
Figure 2B:
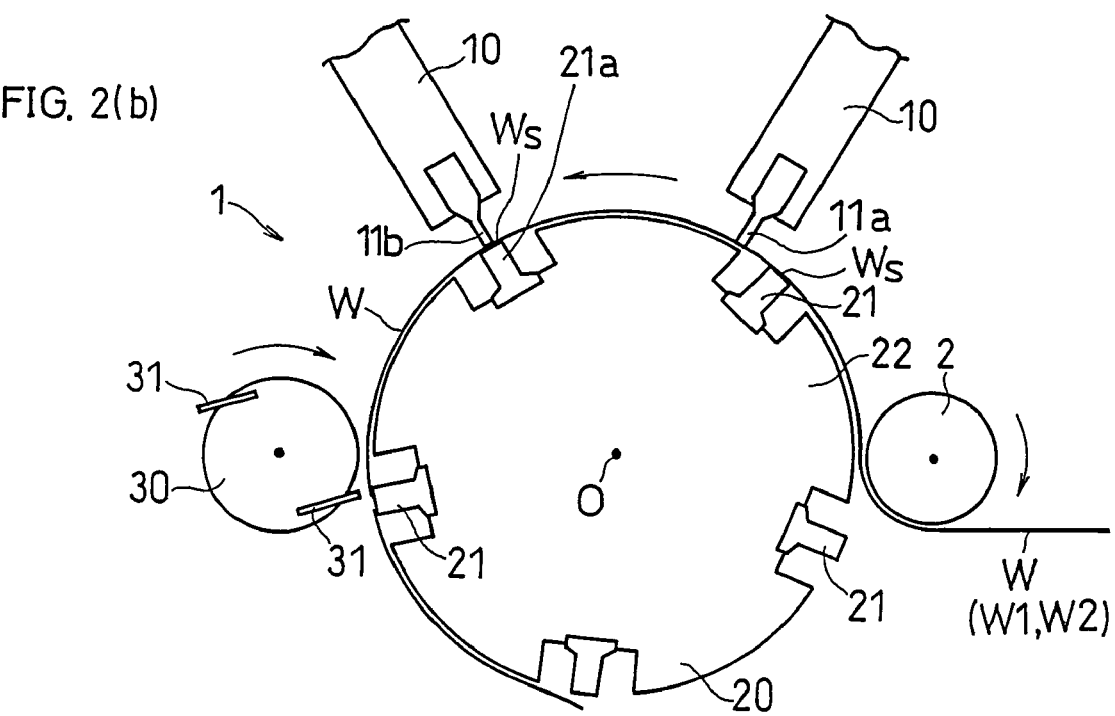

The anvils 21 are provided between the transfer sections 22 spaced apart from one another. The anvil 21 comes close to an upstream horn 11a and then a downstream horn 11b as the drum 20 rotates, as shown in FIGS. 2(a) and 2(b). As shown in FIG. 3, the anvil 21 is protruding radially outward with respect to the transfer section 22, and can thus come in close proximity to the horn 11.

An absorbent body C provided in the sheet-like material W may be located on the transfer section 22. In such a case, the height (distance from the center of rotation O of the drum 20) of the transfer section 22 is preferably lower than the height (distance from the center of rotation O) of the anvil 21. This is for ensuring that the thicker portion of the absorbent body C does not come into contact with the horn 11.

Pillow portions 22a, which are protruding radially outward with respect to the periphery of the transfer section 22, may be provided at opposite ends of the transfer section 22. This is for preventing the sheet-like material W from being bent and damaged by the step between the anvil 21 and the transfer section 22. The height of the pillow portions 22a may be lower than the height of the anvil 21.

Figure 4:
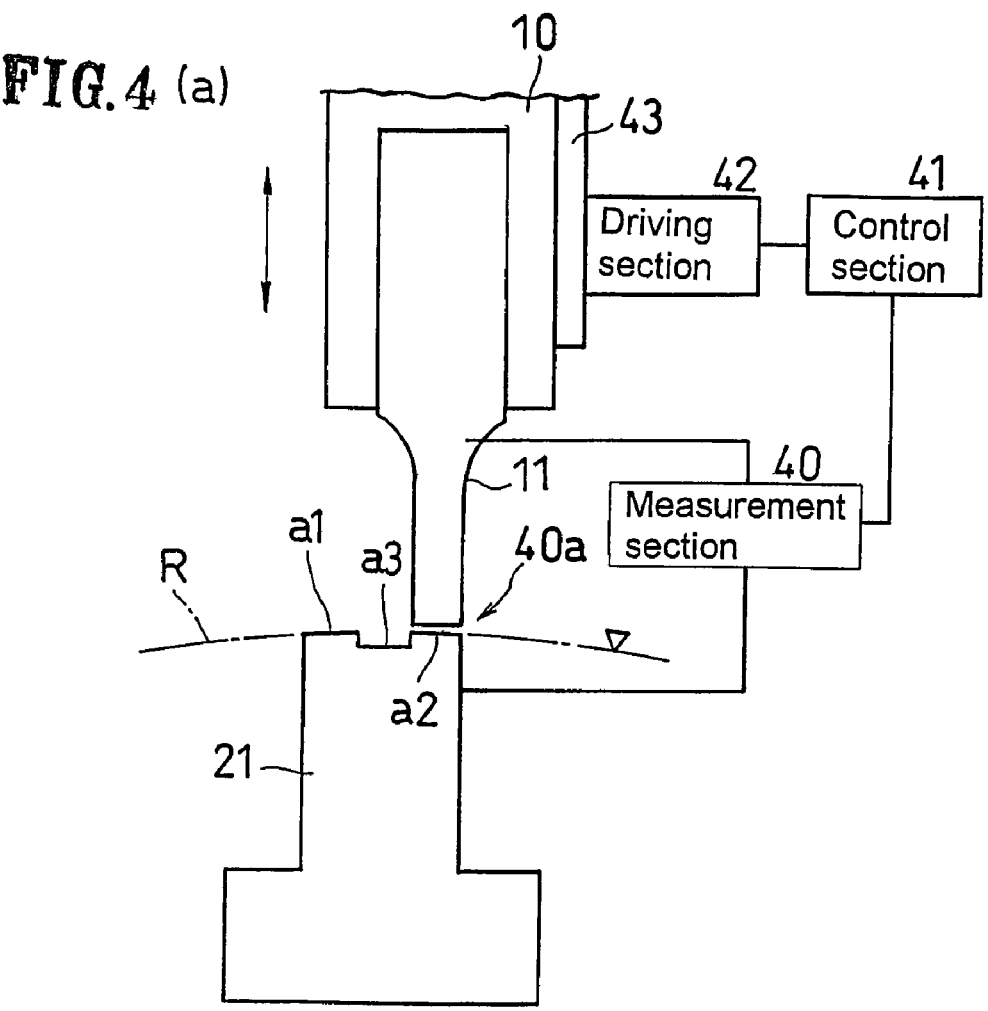
FIG. 4(a) is a schematic diagram showing a mechanism for controlling a horn and an anvil.
FIG. 4(b) is a schematic cross-sectional view showing an alternative example of an anvil.
Figure 4:
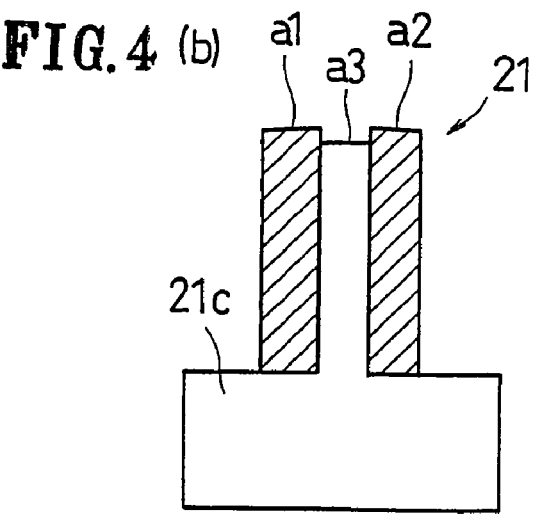

As shown in FIG. 4(a), when the anvil 21 comes close to the horn 11, the energy from the ultrasonic vibrations of the horn 11 is applied to a welding target portion $W_T$ (FIG. 5) of the sheet-like material W, thereby heating the welding target portion $W_T$.

Note that the distance between the anvil 21 and the tip of the horn 11 is exaggerated in various figures for the purpose of illustration.

For example, the ultrasonic horn 11 may be an ultrasonic horn described in Japanese National Phase PCT Laid-Open Publication No. 10-513128 (WO96/23645). As is well known in the art, a seal pattern including many protruding portions may be formed on the surface of the horn 11. Alternatively, a seal pattern may be formed on the surface of the anvil 21, instead of forming a seal pattern on the surface of the horn 11.

As shown in FIG. 4(a), the anvil 21 may include a first portion a1 and a second portion a2 for receiving vibrations from the horn 11, and a third portion a3 for receiving the cutter 31 (FIG. 1). The third portion a3 is located between the first portion a1 and the second portion a2. The first portion a1, the third portion a3 and the second portion a2 are arranged in this order in the circumferential direction of the drum 20. As the drum 20 (FIG. 1) rotates, the first portion a1, the third portion a3 and the second portion a2 of the anvil 21 pass by the horn 11 in this order.

Where the anvils 21 rotate together with the drum 20 about the center of rotation O shown in FIG. 3, a first distance r1 from the center of rotation O to the first portion a1 is set to be generally equal to a second distance r2 from the center of rotation O to the second portion a2. Note that the first distance r1 and the second distance r2 are set to be generally equal to each other for all of the anvils 21.

The first and second distances r1 and r2 are set to be greater than a third distance r3 from the center of rotation O to the third portion a3. Thus, the third portion a3 for receiving the cutter 31 is depressed toward the center of rotation O with respect to the first portion a1 and the second portion a2 for receiving vibrations from the horn 11. In other words, the tip portion of the anvil 21 is generally in a concave shape.

Thus, since the anvil 21 includes the first portion a1, the second portion a2 and the third portion a3, the pair of welded areas Ws and Ws are welded together by the first portion a1 and the second portion a2, while forming a non-welded area Wc between the welded areas Ws and Ws, as shown in FIG. 5(a).

As shown in FIG. 4(a), the surface of the first portion a1 and that of the second portion a2 may be formed in an arched shape that generally conforms with an arc R about the center of rotation O (FIG. 3). This is for achieving desirable welding.

The anvil 21 may be formed by three members, for example, as shown in FIG. 4(b). Specifically, the anvil 21 may include an anvil main body 21c including the third portion a3, and the first and second portions a1 and a2, being separate members, which are fixed on opposite sides of the anvil main body 21c.

The present device is provided with a sensor for measuring the distance between the anvil 21 and the horn 11 in a state where the anvil 21 and the horn 11 are facing each other.

The sensor may be, for example, a capacitive sensor for measuring the distance by measuring an electric capacitance, as will be described below.

As shown in FIG. 4(a), the anvil 21 and the horn 11 are connected to each other via a measurement section (sensor) 40 by means of a conductive line. The anvil 21 and the horn 11 together form a capacitor 40a having a predetermined electric capacitance when facing each other with a predetermined interval therebetween.

The measurement section 40 measures a predetermined physical quantity according to the electric capacitance of the capacitor 40a, and calculates the distance (the size of the gap) between the anvil 21 and the horn 11 from the physical quantity. The physical quantity to be measured may be the frequency of the oscillation circuit, or the charged voltage or the charge time of the capacitor 40a.

The measurement section 40 is connected to a control section 41 via an interface (not shown), and outputs the calculated distance to the control section 41.

The horn 11 is held by a slide base 43 via the welder 10, and can move in the radial direction toward the center of rotation O. The horn 11, together with the slide base 43, is moved in the radial direction by a driving section 42. The control section 41 controls the motor of the driving section 42 by comparing the measured distance information received from the measurement section 40 with a predetermined reference value. Specifically, the motor of the driving section 42 is controlled so that the horn 11 comes closer to the anvil 21 when the measured distance is greater than the reference value, whereas the driving section 42 is controlled so that the horn 11 moves away from the anvil 21 when the distance is smaller than the reference value. Thus, the control section 41 controls the driving section 42 based on the distance information from the measurement section 40 so that the interval (gap) comes closer to a predetermined reference value. Variations in the interval between the horn 11 and the anvil 21 are caused by, for example, the tip surface of the horn 11 wearing down by contacting the sheet-like material, or by the vibrations of the horn 11.

Instead of using a capacitive sensor as described above, any other suitable type of a sensor can be employed as the sensor. For example, the distance between the anvil 21 and the horn 11 may be measured by an optical distance sensor. Alternatively, a voltage may be applied between the anvil 21 and the horn 11, and the distance may be measured by measuring the resulting current flow.

Figure 5:
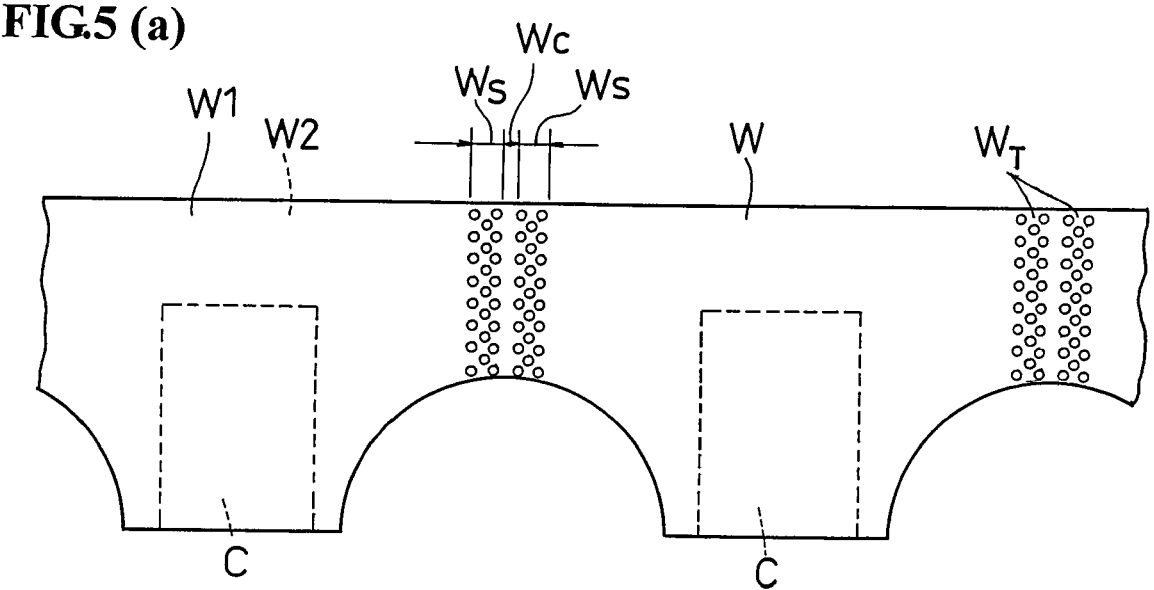
FIGS. 5(a) and 5(b) are plan views showing an example of a sheet-like material.
Figure 5:
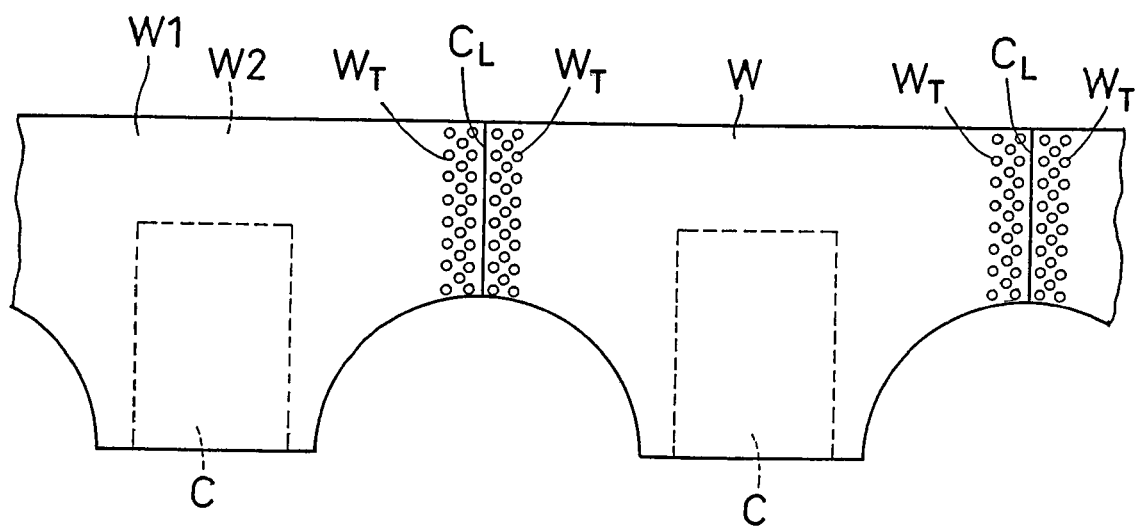

Now, the operation of the welding device will be described. As shown in FIG. 2(a), as the drum 20 rotates to a position where one anvil 21a of the anvils 21 faces the upstream horn 11a, a portion of the sheet-like material W on the anvil 21a is welded ($W_T$ in FIG. 5) by the upstream horn 11a, thus forming the welded areas Ws. Thus, as the anvil 21a passes by the horn 11a, the welded areas Ws are formed on opposite sides of the non-welded area Wc as shown in FIG. 5(a).

Then, as shown in FIG. 2(b), as the drum 20 rotates to a position where the anvil 21a faces the downstream horn 11b, the welded areas Ws, which have been welded by the upstream horn 11a, are further welded (FIG. 5) on the anvil 21a by the downstream horn 11b. Thus, as the anvil 21a passes by the horn 11b, portions on opposite sides of the non-welded area Wc are welded again ($W_T$), as shown in FIG. 5(a). The sheet-like material W as shown in FIG. 2(b) is under a constant tension, and is also held by the transfer section 22. Therefore, the sheet-like material W will not slip on the anvil 21, whereby the same portions of the sheet-like material W can be welded by the two horns 11a and 11b. Thus, even if the strength of the weld given by the horn 11a to the sheet-like material W does not satisfy a predetermined welding strength, the same portions can be welded by the horn 11b to obtain the predetermined welding strength. With the configuration described above, similar effects can be obtained also when there are three or more horns.

When the anvil 21 comes close to the horn 11, the interval between the anvil 21 and the horn 11 as shown in FIG. 4(a) is measured by the measurement section 40, and the measured value is transmitted to the control section 41. Based on the measured value, the control section 41 controls the driving section 42 so as to keep the interval between the horn 11 and the anvil 21 at a predetermined distance.

Then, when the anvil 21 faces the cutter roller 30 as shown in FIG. 1 (i.e., when the drum 20 rotates to a position where the sheet-like material W can be cut by the cutter 31), the cutter 31 of the cutter roller 30 comes into contact with the third portion a3 of the anvil 21, thus cutting a portion (non-welded area Wc) between the two welded area Ws. At this point, the first portion a1 and the second portion a2 of any other anvil 21 are not facing the horn 11.

Thus, while the sheet-like material W (the first and second webs W1 and W2) is being welded by the anvil 21 and the horn 11, it is not cut by the cutter 31. Therefore, variation of the interval between the anvil 21 and the horn 11 varies due to the vibration from the cutting can be prevented. Moreover, since there is no vibration from the cutting when the interval between the anvil 21 and the horn 11 is being measured during the welding process where the horn 11 and the anvil 21 are facing each other, the measurement by the measurement section 40 has a high reliability. Therefore, since the distance between the anvil 21 and the horn 11 can be kept at an appropriate, predetermined distance, the sheet-like material W can be welded desirably.

After being cut by the cutter 31, the sheet-like material W is received by the take-out roller 3 and transferred downstream.

While preferred embodiments of the present invention have been described above with reference to the drawings, obvious variations and modifications will readily occur to those skilled in the art upon reading the present specification.

For example, worn articles produced in a so-called "lateral flow process" or "longitudinal flow process" may be welded. A portion of a sheet-like material, which has been cut into a size of an individual product, may be welded.

Thus, such variations and modifications shall fall within the scope of the present invention as defined by the appended claims.

INDUSTRIAL APPLICABILITY

The present invention is applicable to a device for welding and cutting various types of products or semi-finished products, such as building materials or medical materials, as well as disposable worn articles.

The invention claimed is:

1. A welding device for welding a layered portion where a first web and a second web are layered together, the welding device comprising:
    a drum rotating about an axis;
    a transfer section provided on a periphery of the drum to rotate together with the drum for transferring the first and second webs while holding the first and second webs thereon;
    an anvil provided on the periphery of the drum and extending generally in a direction of the axis for rotating together with the drum;
    a horn provided close to the periphery of the drum, which, together with the anvil, applies a vibration energy to the layered portion;
    a cutter provided close to the periphery of the drum, which comes into contact with the anvil to cut the first and second webs;
    a sensor for measuring a distance between the anvil and the horn; and
    a control section for controlling a relative positions of the anvil and the horn based on the measured distance between the anvil and the horn as measured by the sensor,
    wherein while the horn, together with the anvil, applies the vibration energy to the first and second webs, the cutting of the first and second webs by the cutter is not performed.

2. A welding device according to claim 1, wherein:
    the anvil includes a first portion and a second portion for receiving vibrations from the horn, and a third portion for receiving the cutter, the third portion being located between the first portion and the second portion; and
    the first portion, the third portion and the second portion are arranged in this order in a circumferential direction of the drum.

3. A welding device according to claim 2, wherein a distance from a center of rotation of the anvil to the first portion is generally equal to a distance from the center of rotation to the second portion.

4. A welding device according to claim 2, wherein a distance from a center of rotation of the anvil to the first portion and that from the center of rotation to the second portion are longer than that from the center of rotation to the third portion.

5. A welding device for welding a layered portion where a first web and a second web are layered together, the welding device comprising:
    a transfer section, which can rotate around an axis, for transferring the first and second webs;
    an anvil extending in a direction of the axis for rotating together with the transfer section;
    a horn for, together with the anvil, applying a vibration energy to the layered portion;
    a sensor for measuring a distance between the anvil and the horn;
    a control section for controlling a distance between the horn and the anvil based on information from the sensor; and
    a cutter for cutting the first and second webs, wherein:
    the anvil and the transfer section can move from a position where the horn is provided to a position where the cutter is provided; and
    while the anvil and the horn weld the first and second webs, the cutting of the first and second webs by the cutter is not performed.

* * * * *